United States Patent [19]

Hogan

[11] 4,433,244
[45] Feb. 21, 1984

[54] APPARATUS FOR IRRADIATING TUBING CONNECTIONS

[75] Inventor: Lawrence R. Hogan, Lake Villa, Ill.

[73] Assignee: Baxter Travenol Laboratories, Inc., Deerfield, Ill.

[21] Appl. No.: 359,740

[22] Filed: Mar. 19, 1982

[51] Int. Cl.³ .................... A61L 2/10; G21K 5/08; H01J 37/20

[52] U.S. Cl. .................... 250/455.1; 250/492.1; 422/24; 422/300

[58] Field of Search .......... 250/455.1, 492.1, 493.1, 250/504 R; 604/29; 422/24, 300

[56] References Cited

U.S. PATENT DOCUMENTS

| | | | |
|---|---|---|---|
| 1,896,379 | 2/1933 | Ross | 422/24 X |
| 3,261,660 | 7/1966 | Wilkinson | 422/300 X |
| 3,994,686 | 11/1976 | Rauser et al. | 250/504 X |
| 4,242,310 | 12/1980 | Greff et al. | 422/300 |
| 4,256,952 | 3/1981 | Thomas et al. | 422/300 X |

*Primary Examiner*—Alfred E. Smith
*Assistant Examiner*—Jack I. Berman
*Attorney, Agent, or Firm*—Paul C. Flattery; Garrettson Ellis

[57] ABSTRACT

Apparatus for irradiating a connected pair of tubing ends for antibacterial effect thereon. A housing carries an antibacterial radiation source such as an ultraviolet bulb. Drawer means is slidable into and out of the housing, the drawer means defining vertical slots in opposed side walls thereof having open upper ends for receiving and positioning the connected tubing ends in the drawer means when the drawer means is in open position, and for moving the tubing ends into proximity with the antibacterial radiation source by closing the drawer means.

17 Claims, 9 Drawing Figures

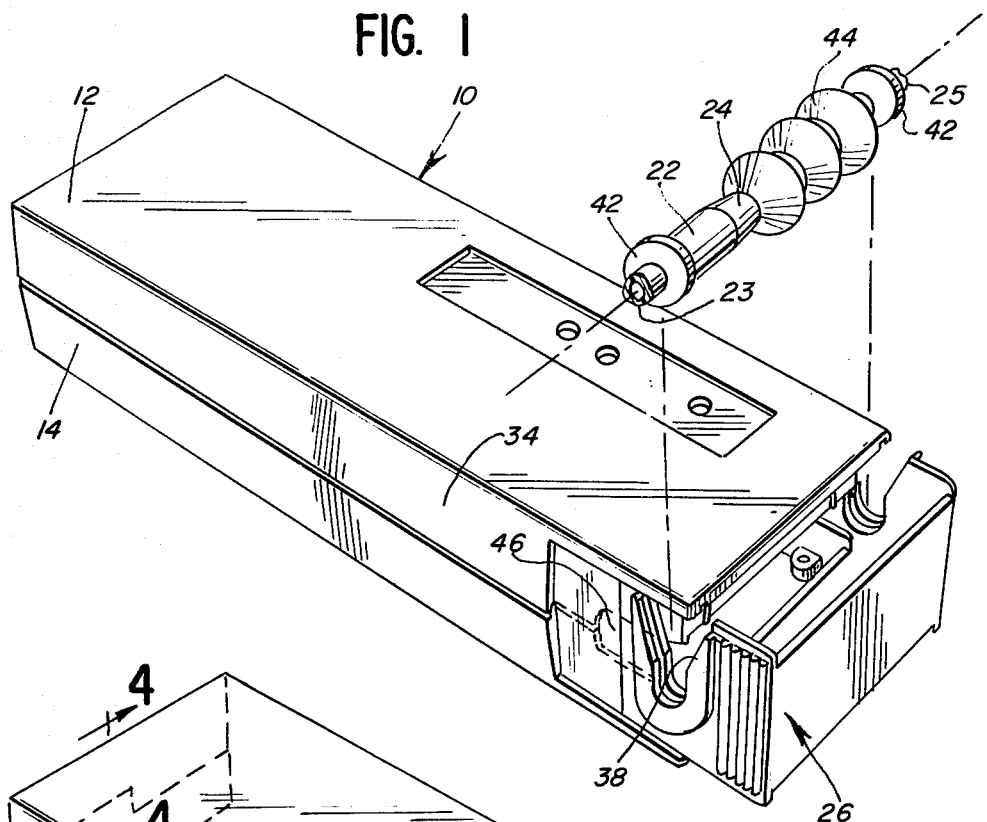
FIG. 1
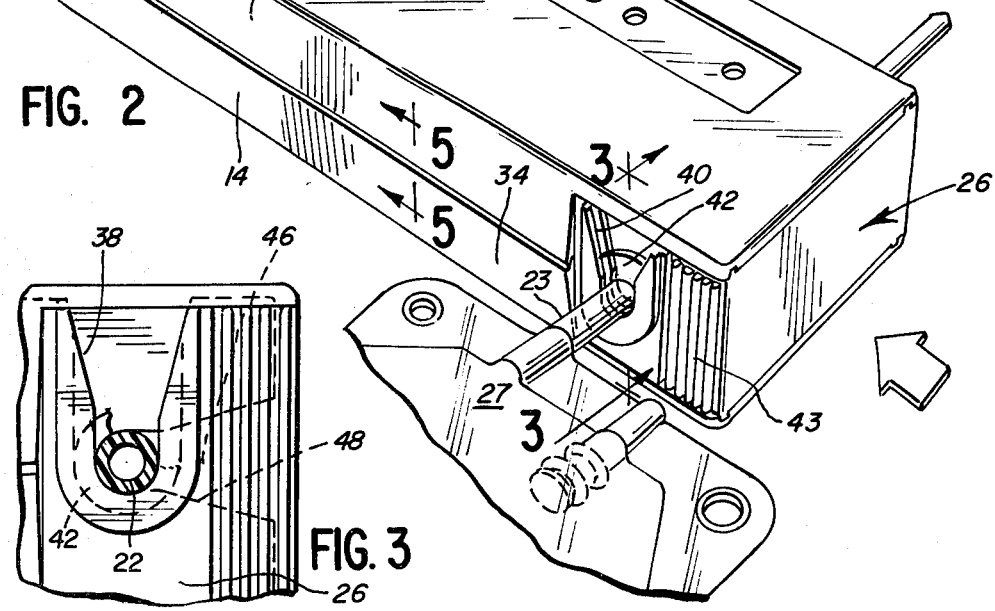
FIG. 2
FIG. 3

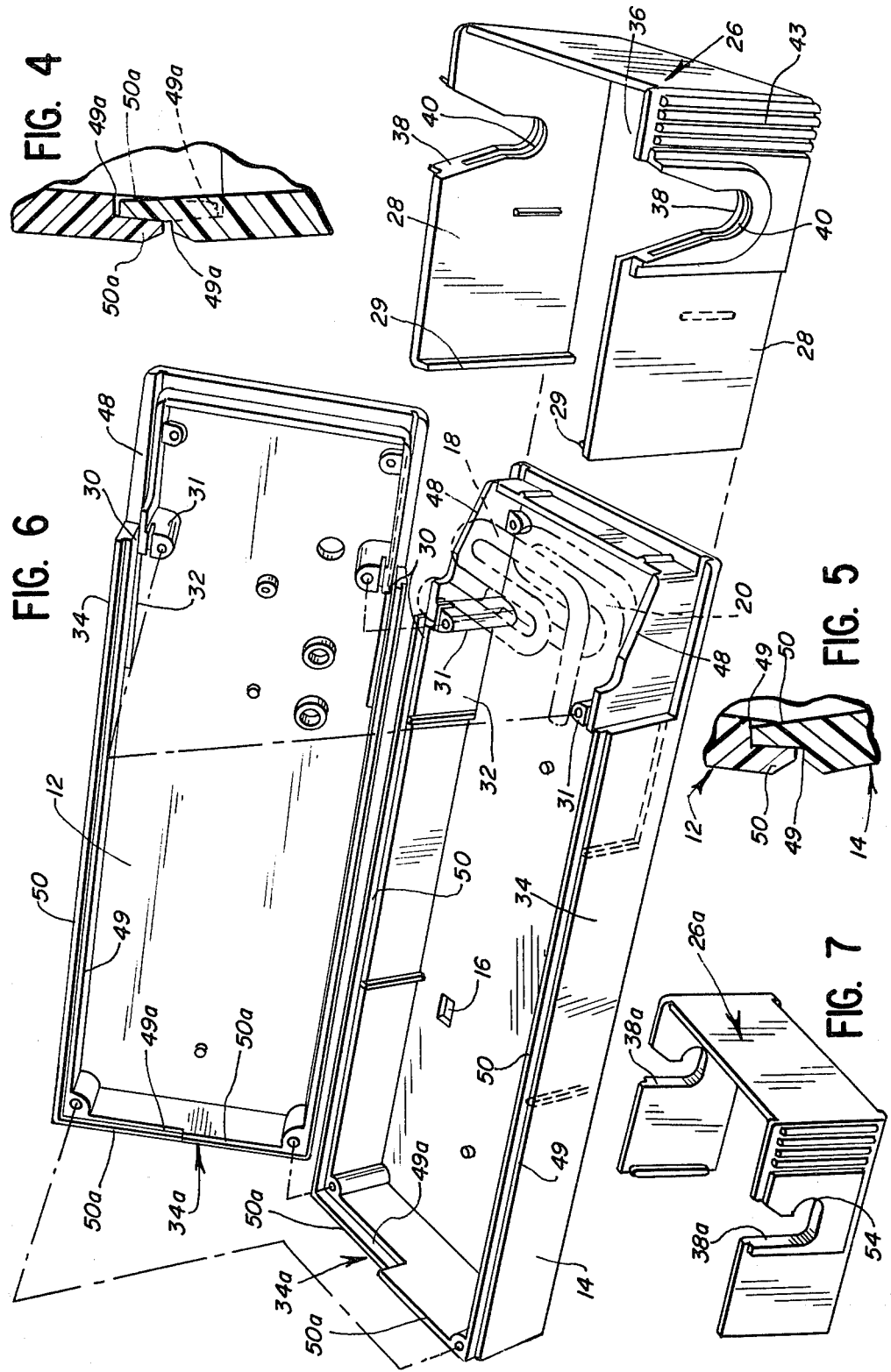

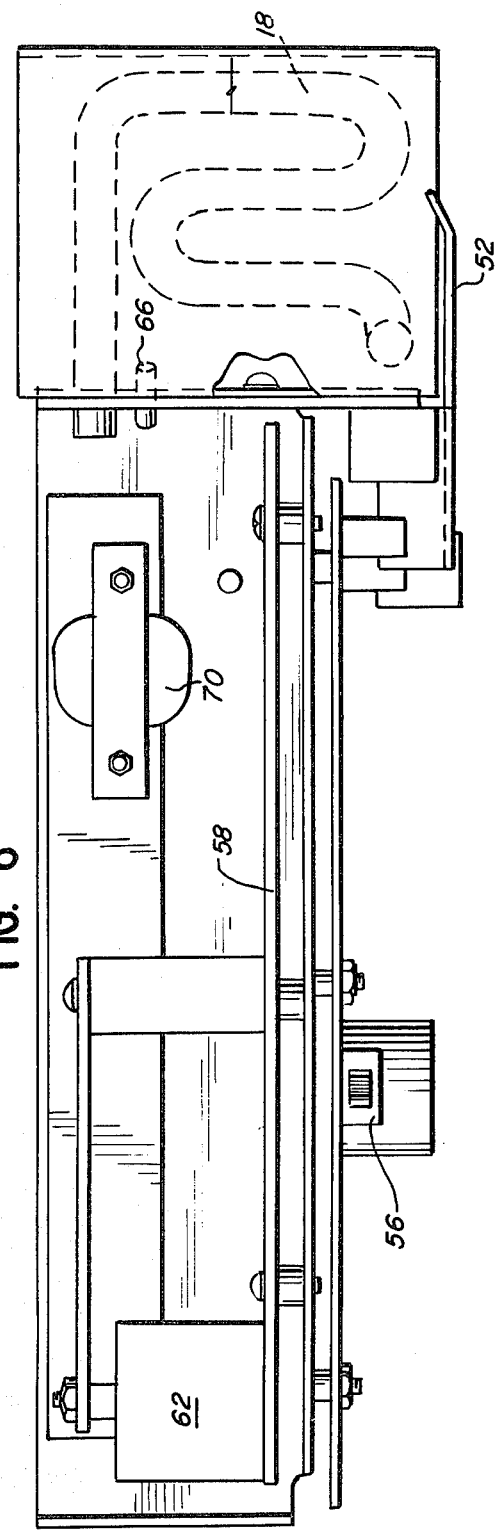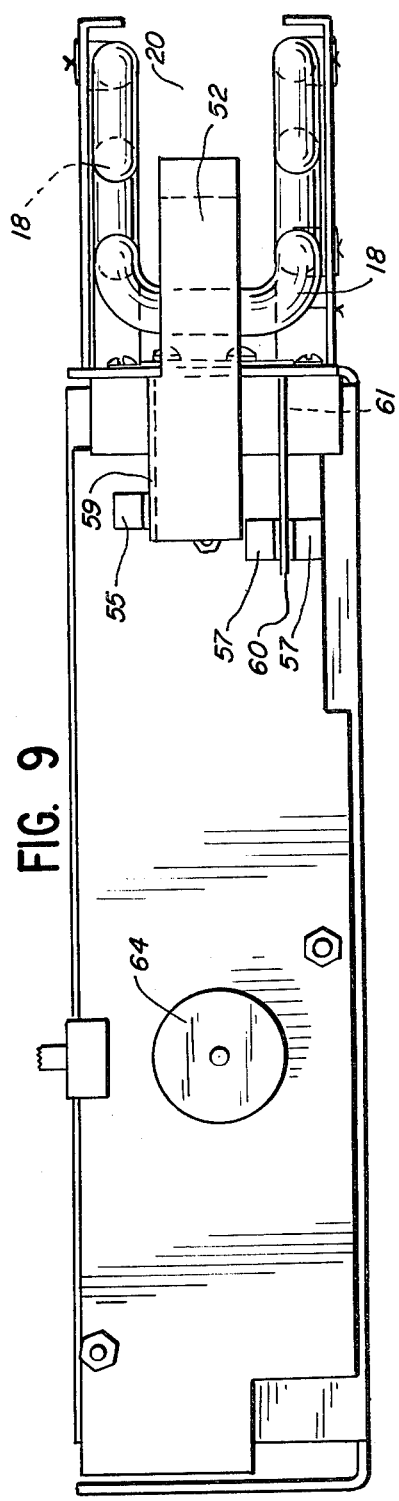

APPARATUS FOR IRRADIATING TUBING CONNECTIONS

TECHNICAL FIELD

There is a need for making connections between various flow conduits or tubings to provide a substantially sterile connection, for example in the field of peritoneal dialysis, where it is important in order to avoid the side effect of peritonitis, which tends to occur in patients undergoing chronic peritoneal dialysis on a daily basis.

DESCRIPTION OF PRIOR ART

It has been previously suggested to connect tubing ends between a source of peritoneal dialysis solution and a set which connects in flow communication with the peritoneal cavity of a patient, for example by fabricating at least portions of the tubing ends out of ultraviolet-transparent material, and exposing the connected ends to ultraviolet irradiation after they have been connected. See, for example, Kulin, et al. patent application Ser. No. 270,743, filed June 5, 1981, which discloses apparatus for ultraviolet irradiation of such tubing connections with a convoluted ultraviolet light tube. Kulin U.S. application Ser. No. 329,163, filed Dec. 10, 1981, discloses another ultraviolet sterilizable connector. Likewise, Popovich et al. patent application Ser. No. 270,800, filed June 5, 1981, and U.S. Pat. No. 4,242,310 both disclose apparatus for providing ultraviolet irradiation of tubing ends, particularly in the field of peritoneal dialysis.

It is desirable for the source of ultraviolet light used to exert antibacterial effect on a freshly made connection between two connected conduits to be very reliable, so that a routine process of ultraviolet exposure can reliably provide the desired and expected level of antibacterial effect, particularly so that the system can be used by patients at home. The source of ultraviolet light must have a means for precisely positioning the tubing connection so that the tubing connection will be exposed to ultraviolet light from essentially all angles, to avoid any shadowed or shaded areas in the tubing connection. Similarly, the device should prevent the leakage of ultraviolet light to the exterior, since a very intense amount of ultraviolet light is used in the process from which the persons in the vicinity should be protected. Finally, the system is desirably simple and capable of use by a relatively untrained patient in the event of its use in continuous ambulatory peritoneal dialysis or similar technique.

In accordance with this invention, a simple, reliable ultraviolet light source meeting the above requirements is disclosed for providing as needed, on a routine basis, the desired and expected antibacterial effect for at least substantial sterilization of the connected ends of two conduits, prior to allowing fluid to flow therethrough. Thus, a substantially sterile connection may be achieved between the peritoneal cavity of a patient, for example, and a container of peritoneal dialysis solution.

DESCRIPTION OF INVENTION

In accordance with this invention, apparatus is provided for irradiating a connected pair of tubing ends for antibacterial effect therein. A housing carries an antibacterial radiation source, typically a source of ultraviolet radiation, but alternatively a high voltage corona discharge source or other antibacterial radiation.

Drawer means are slidable into and out of the housing, with the drawer means defining a pair of vertical slots in opposed side walls, having open upper ends for receiving and positioning the connected tubing ends in the drawer means when the drawer means is in open position, and for moving the tubing ends into proximity with the antibacterial radiation source by closing of the drawer means. Preferably, the drawer means comprises only side walls, without top and bottom walls.

The radiation source may be preferably a convoluted, ultraviolet light bulb which defines a slot for receiving the connected pair of tubing ends, with sections of the ultraviolet light bulb positioned on opposite sides of the slot. Thus the irradiation from the ultraviolet source can impinge the tubing connection from many directions to avoid any shadowed or shaded areas where the irradiation process would be less effective.

Opposed side walls of the housing typically lie against the side walls of the drawer means, with the housing side walls defining horizontal slots which intersect the vertical slots of the drawer means when the drawer means is closed. This intersection of the horizontal and vertical slots defines opposed apertures through which the tubing ends can extend, being positively positioned by said apertures.

This technique provides ease of installation of the tubing by simply manually dropping it into the opposed, vertical slots of the drawer means. Then, as the drawer means is closed, the tubing ends also slide into the horizontal slots, causing them to be precisely positioned in the aperture defined thereby, and resulting in the prevention of leakage of substantial amounts of ultraviolet light outwardly from the housing around the tubing.

The housing may comprise a pair of substantially identical hollow halves joined together at their edges. The edges may define asymmetically positioned steps and flanges, the result of this being that the flanges of the respective hollow halves at the joined edges overlap to block leakage of radiation from the source of antibacterial radiation.

The vertical slots of the drawer means may define channels along their inner periphery to each receive a flange carried by one of the connected pair of tubing ends. This serves to retain the tubing ends in a fixed position while carried in the drawer means of the apparatus of this invention.

DESCRIPTION OF DRAWINGS

In the drawings,

FIG. 1 is a perspective view of the irradiating apparatus of this invention, with its drawer shown in an open position and with a pair of connected conduits about to be installed in the drawer for irradiation.

FIG. 2 is a perspective view of the apparatus of this invention with the pair of connected conduits installed in the drawer, and the drawer in closed, irradiating position.

FIG. 3 is a fragmentary elevational view taken along line 3—3 of FIG. 2, with the tubing of the connected conduits shown in section.

FIG. 4 is a fragmentary, sectional view of the side wall at the end of the housing, taken along line 4—4 of FIG. 2.

FIG. 5 is a fragmentary, sectional view of the side wall of the apparatus, taken along line 5—5 of FIG. 2.

FIG. 6 is a fragmentary perspective view of the apparatus of this invention, showing an opened housing with most electrical components removed for clarity, and showing the convoluted ultraviolet light source utilized in the apparatus, the drawer means being also removed from normal engagement.

FIG. 7 is a perspective view of an alternative drawer means for use in this invention.

FIG. 8 is a bottom plan view of the apparatus of this invention without its housing.

FIG. 9 is an elevational view of the apparatus of this invention without its housing.

DESCRIPTION OF SPECIFIC EMBODIMENT

Referring to the drawings, FIG. 1 shows UV (ultraviolet) box 10 which carries a housing made of a pair of mating housing halves 12, 14 which may be a pair of substantially identical shells for simplicity of manufacture. Shell 14 may have formed in it an aperture 16 (FIG. 6), and other modifications may be made as desired. As shown in FIG. 6, shells 12, 14 carry convoluted UV bulb 18, which defines slot or channel 20 (seen best in FIG. 9) for receiving the connected pair of tubing ends 22, 24 therein so that sections of UV bulb 18 are positioned on opposite sides of the slot for irradiation thereof from many different positions. The tubing upon which tubing ends 22, 24 are carried is omitted for purposes of clear disclosure.

Drawer 26 is provided, defining a pair of sliding walls 28 which slide in slots 30 (FIG. 6) defined between inner side wall 32 and outer side wall 34 of each housing half or shell 12, 14. Drawer 26 has an open bottom 36 as shown, and also defines a pair of vertical slots 38, having open upper ends as shown in FIG. 6, in opposed sidewalls 28 for receiving tubing ends 22, 24. Each of slots 38 in drawer 26 defines a slot 40 for receiving a flange 42 of one of the connected tubing ends 22, 24, so that, as shown for example in FIG. 2, the connected tubing ends 22, 24 may be firmly retained in a desired position in drawer 26.

Connected tubing ends 22, 24 may constitute an arrangement known from the previously cited patent applications of a spike carried by one of the tubing ends intended to penetrate a diaphragm carried by the other tubing end, with a bellows 44 permitting advancement of the spike through the diaphragm after the tubing ends have been connected. Thus the tubing ends can be treated with ultraviolet radiation in the apparatus of this invention, and the diaphragm can then be opened to permit flow through the respectively joined tubings.

The connected tubing ends 22, 24 are placed into the open drawer 26, and drawer 26 may be closed as shown in FIG. 2. Housing halves 12, 14 define between them a horizontal slot 46 on each side of the sidewalls 34, so that each horizontal slot 46 intersects the adjoining slot 38, as shown particularly in FIG. 3, with the effect that each tubing end 22 is captured in an aperture defined by the junction of the two slots 38, 46. Slots 46 are defined by angled surfaces 48, which provide a tapering slot 46 as shown for convenience in positioning of tubing ends 22, 24. Vertical slots 38 may also be tapered in similar manner, beginning with a wide mouth and terminating with a relatively constricted inner end.

With drawer 26 being closed, tubing ends 22, 24 are positioned in channel 20 in precisely the desired location, being automatically positioned by the interaction of slots 38, 46 as drawer 26 is closed. Thus the user does not have to be concerned about proper positioning, since it will take place automatically if flanges 42 are properly positioned in the channel 40 of vertical slots 38.

Ridges 43 are provided on both sides of drawer 26 for manual gripping purposes.

Drawer 26 is shown to have detent members 29 for releasable retention against posts 31 to limit the opening of the drawer thus avoiding its accidental loss. Drawer 12 may be removed by opening the two halves of the apparatus 12, 14, pulling drawer 26 out and replacing it with a substitute as may be desired.

The sidewalls 34 of housing halves, 12, 14 preferably define edges which in turn define asymmetrically positioned steps 49 and flanges 50. Because of the asymmetric positioning, the two substantially identical housing halves 12, 14 can be closed upon each other, with flanges and steps assuming the relationship shown for example in FIG. 5, whereby ultraviolet light leaks are substantially eliminated. With respect each to sidewall 34a, which could also be viewed as the end wall, a pair of flanges 50a and associated steps 49a are provided (FIGS. 4 and 6) with one of the flanges 50a being inside of its step 49a along half of the width of each housing half, and the other flange 50a being outside of its corresponding step 49a, so that as the housing halves are brought together the various flanges 50a and steps 49a mate together to form a UV light blocking junction despite the identical configuration of the two housing halves 12, 14.

As shown in FIGS. 8 and 9, sensing switch actuator 52 may interact with drawer means 26 to be pushed to the left to actuate switch 55 when the drawer is closed. Optical switch 55 may be a commercial optical switch sold by TRW, Inc. Drawer switch actuator 60 is also provided. Accordingly, two sets of switches indicate the closing of drawer 26. Apertures 59 are provided and move with switch actuators 52, 60 so that the optical switches 55, 57 are actuated by the proper positioning of switch actuator 52.

Springs compress as actuator 52 moves into the drawer-closed position, biasing actuator 52 into a drawer-open position so that it spontaneously opens when the drawer is open, disabling the electrical operation of the device.

Referring to FIG. 7, a different design of drawer is disclosed in which vertical slot 38a defines an enlarged portion 54 at its inner area for receiving tubing ends 22, 24. Because of enlarged portion 54, drawer 26a can close further, and this configuration tends to eliminate a corner light leak adjacent the tubing ends. If desired, a channel analogous to channel 40 may be used in vertical slots 38a for receiving and holding flanges similar to flanges 42 of the tubing ends. Otherwise, this drawer 26a may be identical to drawer 26.

An advantage of this invention is that the various drawers 26, 26a may be replaced as desired to accommodate various shapes of tubing ends 22, 24 each drawer 26, 26a being a relatively simple piece of plastic, so that the apparatus of this invention can be used with a large number of different designs of connected tubing ends.

Referring particularly to FIGS. 8 and 9, the electronics and electrical supply system carried in the apparatus of this invention may be of any desired design for providing a desired current and voltage to UV bulb 18. The particular electronics used herein do not constitute the invention of this application.

Basically, the electronics may also include, if desired, a failure mode test switch so that the user can determine the operability of the system, and an audible cycle-complete switch, when desired to indicate to the user that the sterilization cycle is complete.

Conventional safety interlocks may be used so that the UV bulb 18 is shut off if drawer 26 is opened. Also, other features as discussed in the previously described patent applications may be utilized in the apparatus of this invention as may be desired. Particularly, the chamber surrounding UV bulb 18 may carry a reflective aluminum coating to reflect ultraviolet light around the chamber for improved antibacterial effect. Likewise, a system may be provided which is dose responsive, so that the UV bulb is shut off when a predetermined dose of ultraviolet light has been emitted, in a manner independent of time.

Switch 56 projects through aperture 16, and serves as a three position switch, which three positions include a test position by which the system may be tested for operativeness, a sonic alarm "on" position and a sonic alarm "off" position, so that the complete cycle may be indicated by a visual indicator light or a sonic buzzer as desired.

Printed circuit board 58 is provided for the desired logic for the system, and output transformer 60 and inductor 62 are shown. Buzzer 64 provides the sonic indication, with suitable specific circuitry being readily constructed by those skilled in the art.

Light sensor 66 communicates through a logic circuit with the lamp power supply, controlling the power supply to maintain a set current powering lamp 18, so that the ultraviolet light emitted remains within a desired range of intensities.

The above has been offered for illustrative purposes only and is not intended to limit the scope of the invention of this application, which is as defined in the claims below.

That which is claimed is:

1. In apparatus for irradiating a connected pair of tubing ends for antibacterial effect therein, the improvement comprising, in combination:
    a housing which carries an antibacterial radiation source;
    drawer means slidable into and out of said housing, said drawer means defining a pair of vertical slots in opposed side walls thereof having open upper ends for receiving and positioning said connected tubing ends in the drawer means when the drawer means is in open position, and moving the tubing ends into proximity with the antibacterial radiation source by closing of the drawer means.

2. The apparatus of claim 1 in which said radiation source is a convoluted ultraviolet light bulb which defines a channel for receiving the connected pair of tubing ends, with sections of said ultraviolet light bulb positioned on opposite sides of said channel.

3. The apparatus of claim 1 in which opposed side walls of said housing lie against the side walls of said drawer means, said housing side walls defining horizontal slots which intersect the vertical slots when the drawer means is closed, to define opposed apertures at the intersections of the vertical and horizontal slots through which said tubing ends can extend to be positively positioned by said apertures.

4. The apparatus of claim 1 in which said housing comprises a pair of substantially identical hollow halves joined together at their edges, said edges defining asymmetrically positioned steps and flanges, whereby the flanges of the respective hollow halves at the joined edges overlap to block leakage of radiation from said source.

5. The apparatus of claim 1 in which said vertical slots define channels along their inner peripheries to each receive a flange carried by one of the connected pair of tubing ends, for retaining the tubing ends in a fixed position.

6. The apparatus of claim 5 in which said vertical slots are each tapered to form a narrowed, closed end.

7. The apparatus of claim 6 in which said horizontal slots are each tapered to form a narrowed, closed end.

8. In apparatus for irradiating a pair of connected tubing ends for antibacterial effect therein, the improvement comprising, in combination:
    a housing which carries an antibacterial radiation source;
    drawer means slidable into and out of said housing, said drawer means defining a pair of vertical slots in opposed side walls thereof having open upper ends for receiving and positioning said connected tubing ends in the drawer means when the drawer means is in open position, and moving the tubing ends in proximity with the antibacterial radiation source by closing of the drawer means, said radiation source defining a convoluted ultraviolet light bulb which defines a channel for receiving said connected pair of tubing ends when the drawer means is closed, sections of the ultraviolet light bulb being positioned on opposite sides of the channel for irradiation of the connected pair of tubing ends from a multiplicity of directions, the side walls of said housing lying against the side walls of the drawer means, said housing side walls defining horizontal slots which intersect the vertical slots when the drawer means is closed to define opposed apertures at the intersections of the vertical and horizontal slots through which said tubing ends can extend to be positively positioned by said apertures.

9. The apparatus of claim 8 in which said vertical slots define channels along their inner peripheries to each receive a flange carried by one of the connected pair of tubing ends, for retaining the tubing ends in a fixed position.

10. The apparatus of claim 9 in which said vertical slots are tapered to form a narrowed, closed end.

11. The apparatus of claim 10 in which said housing comprises a pair of substantially identical hollow halves joined together at their edges, said edges defining asymmetrically positioned steps and flanges whereby the flanges of the respective hollow halves at the joined edges overlap to block leakage of radiation from said source.

12. The apparatus of claim 11 in which said horizontal slots are each tapered to form a narrowed, closed end.

13. An apparatus for irradiating a pair of connected tubing ends for antibacterial effect therein, the improvement comprising, in combination:
    a housing which carries an antibacterial radiation source;
    drawer means slidable into and out of said housing, said drawer means defining a pair of vertical slots in opposed side walls thereof having open upper ends for receiving and positioning said connected tubing ends in the drawer means when the drawer means is in open position, and moving the tubing ends into proximity with the antibacterial radiation source by closing of the drawer means, said radiation source defining a convoluted ultraviolet light bulb which defines a channel for receiving said connected pair of tubing ends when the drawer means is closed, sections of the ultraviolet light bulb being positioned on opposite sides of the channel for irradiation of the connected pair of tubing ends from a multiplicity of directions, said housing comprising a pair of substantially identical hollow halves joined together at their edges, said edges defining asymmetrically positioned steps and flanges whereby the flanges of the respective hollow halves at the joined edges overlap to block leakage of radiation from said source.

14. The apparatus of claim 13 in which said vertical slots are tapered to form a narrowed, closed end.

15. The apparatus of claim 1 in which said drawer means has an open bottom.

16. The apparatus of claim 8 in which said drawer means has an open bottom.

17. The apparatus of claim 13 in which said drawer means has an open bottom.

* * * * *